United States Patent [19]

Yudelson

[11] Patent Number: 5,349,957

[45] Date of Patent: Sep. 27, 1994

[54] PREPARATION AND MAGNETIC PROPERTIES OF VERY SMALL MAGNETITE-DEXTRAN PARTICLES

[75] Inventor: Joseph S. Yudelson, Rochester, N.Y.

[73] Assignee: Sterling Winthrop Inc., New York, N.Y.

[21] Appl. No.: 984,611

[22] Filed: Dec. 2, 1992

[51] Int. Cl.$^5$ .............................................. A61B 6/00
[52] U.S. Cl. ..................................... 128/653.4; 424/9; 600/12
[58] Field of Search ........ 128/653, 654, 714, 897–899; 424/1.1, 4, 9, 173, 809; 600/1, 3, 12

[56] References Cited

U.S. PATENT DOCUMENTS

| | | | |
|---|---|---|---|
| 4,101,435 | 7/1978 | Hasegawa et al. | 424/174 |
| 4,735,796 | 4/1988 | Gordon | 128/653.4 |
| 4,795,698 | 1/1989 | Owen et al. | 435/4 |
| 4,975,282 | 12/1990 | Cullis | 424/50 |
| 5,055,288 | 10/1991 | Lewis et al. | 128/653.4 |
| 5,069,936 | 12/1991 | Yen | 424/1.1 |
| 5,204,457 | 4/1993 | Marino et al. | 536/101 |
| 5,219,554 | 6/1993 | Groman et al. | 128/653.4 |

Primary Examiner—John D. Yasko
Assistant Examiner—Chalin Smith
Attorney, Agent, or Firm—William J. Davis

[57] ABSTRACT

The present invention is directed to particles comprised of a magnetically responsive material and a dispersant, said particles having a particle size range of about 2 to about 10 nm. The present invention is also directed to a method for the preparation of such particles comprising admixing a magnetically responsive material with a dispersant to form an admixture, and contacting said first admixture with a base for a time period and under conditions appropriate to form a magnetically responsive material-dispersant particle. In a preferred embodiment, the magnetically responsive material is magnetite, the dispersant is dextran, and the base is ammonium hydroxide. In a further preferred embodiment, the admixture is suspended in a gel phase. The present invention is further directed to a method of diagnosis comprising administering to a mammal a contrast effective amount of these particles suspended or dispersed in a physiologically tolerable carrier and generating an NMR image of said mammal.

11 Claims, 1 Drawing Sheet

PREPARATION AND MAGNETIC PROPERTIES OF VERY SMALL MAGNETITE-DEXTRAN PARTICLES

FIELD OF THE INVENTION

The present invention relates to a diagnostic agent containing particles having a magnetic moment, which diagnostic agent is useful in nuclear magnetic resonance (NMR) imaging, and a method for making that diagnostic agent. The invention further relates to the use of such diagnostic reagents in pharmaceutical compositions.

BACKGROUND OF THE INVENTION

NMR contrast agents in commercial use at the present time are paramagnetic. They consist of transition metals (such as manganese), elements of the lanthanide series (such as gadolinium), or stable organic free radicals. More recently, particles possessing magnetic moments have attracted a great deal of attention because they are effective at concentrations less than one millionth of the effective concentrations of non-particulate materials. Renshaw et al., Magnetic Resonance Imaging 4:351–357 (1986).

In addition, these non-particulate agents affect both the spin lattice ($T_1$) and the spin-spin ($T_2$) relaxation time of protons in different tissues whereas the particulate materials such as the magnetic iron oxides primarily reduce the $T_2$ relaxation time. Josephson et al., Magnetic Resonance Imaging 6:647–653 (1988).

Several reports relate enhanced $T_2$ relaxation rates of normal tissue but not of tumor tissues. By using the $T_2$ weighted image sequence, good contrast can be obtained between the tumor and the surrounding healthy tissue at very low levels of particulate contrast agent. Magin et al., Magnetic Imaging in Medicine 20:1–16 (1991); Weissleder et al., Radiology 162:494–498 (1990); Saini et al., Radiology 167:211–216 (1987); Id. 217–222; Hahn et al., Radiology 164:37–41 (1987).

The size of the magnetic particulates plays a very important role in the selectivity of absorption of contrast agent by tissue. When the diameter of the magnetic particles is in the range of 0.03 to 1 micron (or larger), they are rapidly cleared from the blood by the mononuclear phagocytic system (MPS) of the spleen and liver and no particles are found in other tissues. Weissleder et al. Radiology 175:489–493 (1990). As the sizes of the particles decrease to the 0.01 micron (10 nanometer, nm) range and lower, the particles are not absorbed by the MPS of the liver and spleen and have a longer life-time in the circulatory system and thus have uptake by lymph nodes, bone marrow, and other organs.

Current methods of producing magnetic particles produce a reaction product which possesses a wide range of magnetic particle sizes. The so-called ultrasmall sizes are obtained by fractionation of the reaction mixture. This involves high speed centrifugation, and the use of gel chromatographic columns. U.S. Pat. No. 5,055,288. Such fractionation results in very low yields of the desired product.

Molday et al., J. Immun. Meth. 52:353–367 (1982) describe the preparation of particles in the size range of 30–40 nm which have an electron dense core of 15 nm. Molday uses centrifugation and gel filtration chromatography to fractionate and purify the resulting particles, similar to the methods of U.S. Pat. No. 5,055,288.

Other techniques for the preparation of small magnetite particles for magnetic resonance imaging (MRI) have followed Molday in the use of dextran, with the exception of a liposome based system. U.S. Pat. No. 5,088,499.

U.S. Pat. No. 4,965,007 describes magnetite encapsulated by a gelatin-gum arabic coacervate for magnetic separations. That material is not suitable for MRI by virtue of the physiological limitation imposed by the encapsulating system.

U.S. Pat. No. 4,985,233 describes a method of diagnosis by the administration of a diagnostic agent comprised of a paramagnetic compound carried by a particulate macromolecular product. In one embodiment, carboxymethyl gel beads are swelled in the presence of $FeCl_3.6H_2O$, dried and swelled again in the presence of NaOH. The resulting particles have sizes ranging from 40 to 160 microns.

WO Patent 8903-675-A to Carbomatrix AB describes a method for preparing superparamagnetic particles by combining a carbohydrate polymer, ferric chloride, ferrous chloride and NaOH. The resulting particles are said to have a size range of 0.35 to 1.22 microns.

All of the literature methods for the preparation of magnetite ($Fe_2O_3$) for use as a magnetic resonance contrast agent produce a wide range of magnetic particle sizes. For MRI, the magnetic crystallite size preferably is less than about 10 nm and these are obtained by fractionation of the reaction mixture using high speed centrifugation and gel chromatography.

The present invention describes a new method for the synthesis of particles comprised of a magnetically responsive material and a dispersant in which a very narrow size distribution with a range of about 2 to about 10 nm is obtained without the necessity for fractionation procedures. This process is capable of high yields.

SUMMARY OF THE INVENTION

The present invention is directed to particles comprised of a magnetically responsive material and a dispersant, said particles having a particle size range of about 2 to about 10 nm. Preferably, the particle size range is from about 2 to about 5 nm.

The present invention is also directed to a method for the preparation of such particles comprising admixing a magnetically responsive material with a dispersant to form an admixture, and contacting said first admixture with a base for a time period and under conditions appropriate to form a magnetically responsive material-dispersant particle. In a preferred embodiment, the magnetically responsive material is magnetite, the dispersant is dextran, and the base is ammonium hydroxide. In a further preferred embodiment, the admixture is suspended in a gel phase. A preferred gel phase is formed by gelatin or by polyvinyl alcohol. Contacting may take place in a gas, liquid, or gel phase.

The present invention is further directed to a method of diagnosis comprising administering to a mammal a contrast effective amount of these particles suspended or dispersed in a physiologically tolerable carrier and generating an NMR image of said mammal.

DETAILED DESCRIPTION OF THE INVENTION

Figure 1:
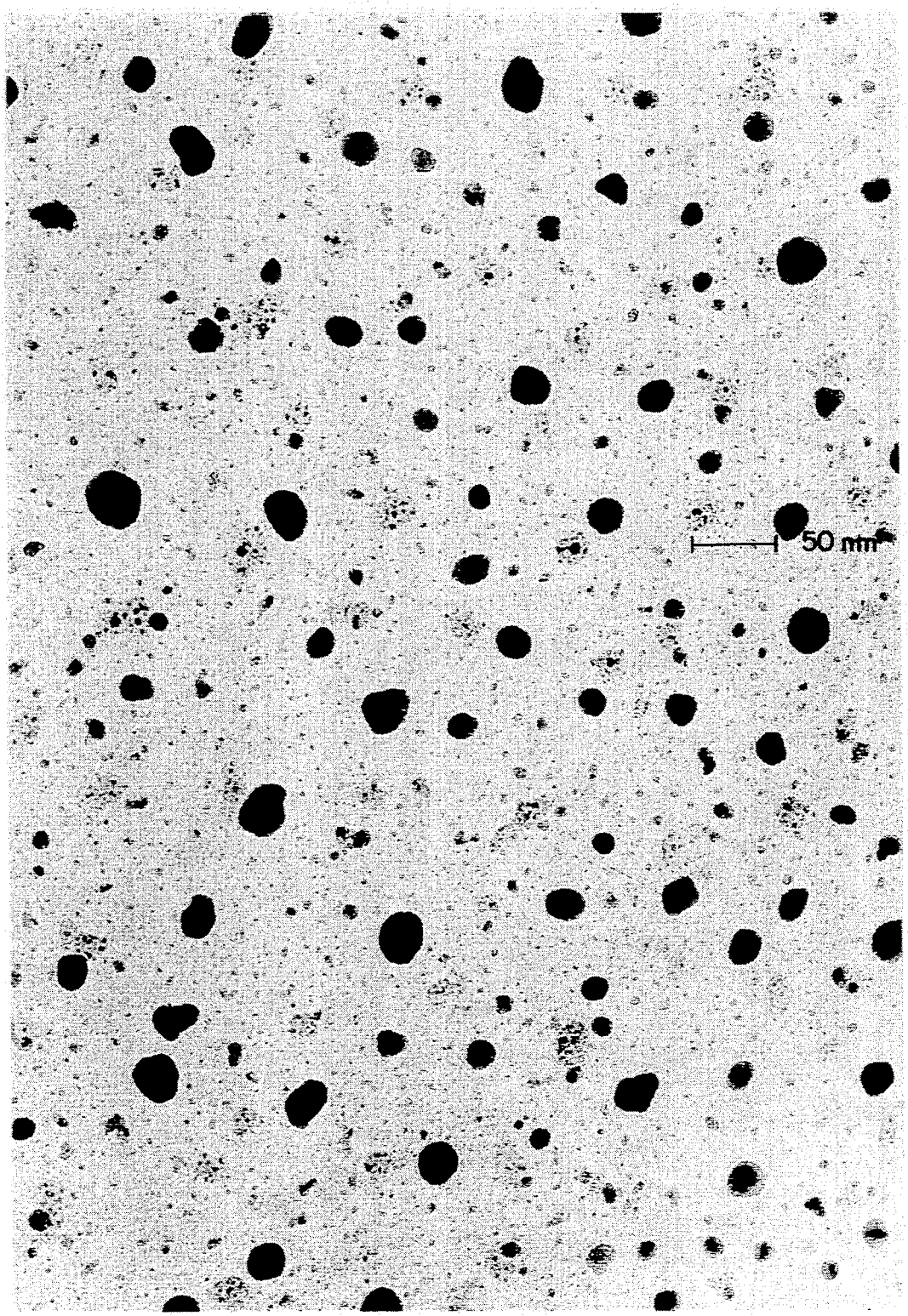
FIG. 1 shows a transmission electron micrograph of particles prepared by the method of Example 3, below. The particles were magnified 279,000 times. The bar indicates 50 nm.

This invention is directed to particles of particle size range from about 2 to about 10 nm, comprised of a magnetically responsive material and a dispersant. These particles are particularly useful as diagnostic agents in NMR imaging.

This invention is also directed to a method by which a base such as ammonium hydroxide is added to an admixture of magnetically responsive material such as an iron salt and a dispersant such as dextran to obtain particles with a diameter in the range of about 2 to about 10 nm. It is necessary to add the hydroxide so that the local hydroxide concentration in the reaction zone is not in excess as the iron oxide product is formed. With alkali metal hydroxides, this may be accomplished by suspending the iron salt-dextran mixture into a gel phase and allowing the hydroxide to diffuse into the gel. In the case of volatile hydroxides, such as ammonium hydroxide, the addition may be made through the gas phase, which is in contact with a solution of the iron salt-dextran.

As used herein, the phrase "particle size" refers to a number average particle size as measured by conventional particle size measuring techniques well known to those skilled in the art, such as sedimentation field flow fractionation, photon correlation spectroscopy, or disk centrifugation. The phrase "particle size range of about 2 to about 10 nm" as used herein means that at least 90 percent of the particles have a weight average particle size of between about 2 nm and about 10 nm when measured by the above-noted techniques. It is preferred that at least 95 percent, and, more preferably, at least 99 percent of the particles have a particle size range from about 2 nm to about 10 nm.

The amount of magnetically responsive material present in the compositions of the present invention depends upon numerous factors, including stability, temperature, pH of the reaction, and the like. A preferred concentration (weight/volume) of magnetically responsive material is from about 0.5 to about 20%, more preferably 1 to 8%.

The magnetically responsive material may be a metal oxide of iron, nickel or cobalt. A magnetic particle particularly useful in the present invention is magnetite ($Fe_3O_4$). This material is prepared by adding alkali to a mixture of ferrous and ferric salts.

The preparation of magnetite is described by equation (1).

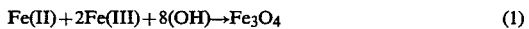

$$Fe(II) + 2Fe(III) + 8(OH) \rightarrow Fe_3O_4 \quad (1)$$

The base, which serves as the hydroxide source (OH), may be either inorganic (for example, sodium, potassium, or ammonium hydroxide) or organic (tetraalkyl ammonium hydroxide).

A dispersing agent (dispersant) is typically present during the reaction. A preferred dispersing agent is dextran. Examples of other dispersing agents include water soluble polysaccharides such as glucans, e.g., starch, amylose, amylopectin (including macromolecular dextrins thereof), glycogen, dextran and pullulan, fructans, e.g., inulin and levan, and other physiologically tolerable polysaccharides of vegetable, microbial or animal origin. Another example is the so called polyglucose obtained by polymerization of glucose. Other examples include macromolecular products obtained by cross-linking carbohydrates or sugar alcohols (e.g., mannitol and sorbitol) with at least one bifunctional cross-linking agent, e.g. with epichlorohydrin or diepoxides or corresponding halogen hydrins. An example of such a product is Ficoll (Pharmacia Fine Chemicals AB, Uppsala, Sweden) which is obtained by cross-linking sucrose with the aid of epichlorohydrin (See, e.g., SE-B-209 018 and U.S. Pat. No. 3,300,474).

The optimal amount of the dispersant can depend, for example, upon the particular magnetically responsive material selected, the critical micelle concentration of the dispersant if it forms micelies, the hydrophilic lipophilic balance (HLB) of the stabilizer, the melting point of the stabilizer, its water solubility, the surface tension of water solutions of the stabilizer, etc. The dispersant preferably is present in an amount of about 0.1–10 mg per square meter surface area of the therapeutic or diagnostic agent. The dispersant can be present in an amount of 0.1–90%, preferably 1–75%, more preferably 10–60%, and most preferably 10–30% by weight based on the total weight of the dry particle.

Dextran was first described for use in oral iron supplements. Ricketts et al., Nature 208:237 (1965). The first mention of its use in stabilizing magnetite particles for use in magnetic resonance imaging appeared in 1978. Ohgushi et al., J. Mag. Reson. 29:599–601 (1978).

In practice, the hydroxide is added to the iron salt-/dextran mixture. Kronick et al, J. Biochem. Biophys. Meth. 12:73–80 (1986) reverse this addition, such that the iron salt-dextran solution is added to an excess of alkali. U.S. Pat. No. 5,102,652 discloses a method where the iron salt solution is added to the alkali-dextran.

The amount of base to be added depends upon a number of factors, including pH of the solution, the nature of the dispersant, the nature of the magnetically reactive material, and the like. A preferred amount of base is an amount sufficient to raise the pH of the suspension to between about 8 and 11.

In one embodiment, the magnetically reactive material-dispersant admixture is suspended in a gel phase. A gel phase, as used herein, is a colloidal suspension of a liquid in a semisolid, that forms a jellylike material. Examples of gelling agents useful in forming a gel phase include porcine skin gelatin, bovine skin gelatin, plant gelatin (such as carageenan), agarose, polyacrylamide, and polyvinyl alcohol. Preferred gelling agents include porcine skin gelatin and polyvinyl alcohol.

The amount of gelling agent useful in the processes of the present invention depends upon numerous factors, including the pH of the solution, the dispersant used, the magnetically reactive material used, the nature of the contacting with the gelled phase, and the like. In a preferred embodiment, the concentration (weight-/volume) of gelling agent is from about 1 to about 10%.

Contacting the magnetically reactive material-dispersant admixture in the liquid phase with the base can be by liquid/liquid or gas/liquid interaction. Where the contacting is by liquid/liquid interaction, the magnetically reactive material-dispersant admixture is contacted with the base by admixing. Where the contacting is by gas/liquid interaction, the magnetically reactive material-dispersant admixture is contacted with the gas phase of a volatile base such as ammonium hydroxide or a volatile amine such as methyl or ethyl amine.

Contacting the magnetically reactive material-dispersant admixture suspended in the gel phase with the base can be by liquid/gel or gas/gel interaction. Where the contacting is by liquid/gel interaction, the gelled magnetically reactive material-dispersant admixture is overlaid with the base. Where the contacting is by gas/liquid interaction, the gelled magnetically reactive material-dispersant admixture is contacted with the gas phase of a volatile base such as ammonium hydroxide or a volatile amine such as methyl or ethyl amine.

In another embodiment, the present invention is directed to a method of diagnosis comprising the administration of a contrast effective amount of these magnetically reactive material-dispersant particles to a mammal.

A contrast effective amount of particles is that amount necessary to provide tissue visualization with magnetic resonance imaging. Means for determining a contrast effective amount in a particular subject will depend, as is well known in the art, on the nature of the magnetically reactive material used, the mass of the subject being imaged, the sensitivity of the magnetic resonance imaging system and the like.

After administration of these particles, the subject mammal is maintained for a time period sufficient for the administered particles to be distributed throughout the subject and enter the tissues of the mammal. Typically, a sufficient time period is from about 20 minutes to about 90 minutes and, preferably from about 20 minutes to about 60 minutes.

The particles are visualized by imaging that tissue with a magnetic resonance imaging system. The visualization of the particles can be accomplished with commercially available magnetic imaging systems such as a General Electric 1.5 T Signa imaging system [$^1$H resonant frequency 63.9 megahertz (MHz)]. Commercially available magnetic resonance imaging systems are typically characterized by the magnetic field strength used, with a field strength of 2.0 Tesla as the current maximum and 0.2 Tesla as the current minimum.

For a given field strength, each detected nucleus has a characteristic frequency. For example, at a field strength of 1.0 Tesla, the resonance frequency for hydrogen is 42.57 MHz; for phosphorus-31 it is 17.24 MHz; and for sodium-23 it is 11.26 MHz.

A carrier or diluent is a material useful for administering the particles and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, the particles of the present invention can be utilized in liquid compositions such as sterile suspensions or solutions, or as isotonic preparations containing suitable preservatives. Particularly well-suited for the purposes of the present invention are injectable media constituted by aqueous injectable isotonic and sterile saline or glucose solutions.

The agents can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are phospholipids and phosphatidyl cholines (lecithins), both natural and synthetic.

Methods of forming liposomes are known in the art. See, for example, Prescott, Ed., *Methods in Cell Biology*, Volume XIV, Academic Press, New York, N.Y. (1976), p. 33 et seq.

The following examples further illustrate the invention and are not to be construed as limiting of the specification and claims in any way.

EXAMPLE 1

Magnetite-dextran particles were produced according to the methods of U.S. Patent Nos. 4,770,183 and 4,827,945 (AMI) and Josephson et al., op. cit. These methods utilize a strong base that is titrated into a reaction mixture consisting of a mixture of iron salts and dextran. After the reaction is completed, the product is centrifuged and fractionated in a gel column. The present example uses sodium hydroxide. A similar synthesis utilizing ammonium hydroxide in place of sodium hydroxide gave similar results, although the amount of magnetite separated by the centrifuge was less.

(i) 3.8 grams of $FeCl_3.6H_2O$ (3.8 g), 1.4 grams of $FeCl_2.4H_2O$ (1.4 g) (both purchased from Aldrich Chemical Company) and 10 grams of dextran (Pharmacia Fine Chemicals) were dissolved in 75 milliliters (ml) of water with stirring via a magnetic stirring bar.

(ii) 80 ml of 1 normal (1N) sodium hydroxide (NaOH) was added over a 30 minute time period, with vigorous stirring. As the base was added, the solution changed in color from black to brown and then green. The final pH value of the solution was approximately 11.5.

(iii) The solution from step (ii) was then heated with stirring to 80° C. at which point the solution was dark brown. At this point, the pH of the solution was rapidly lowered to a value of 7 using 5N hydrochloric acid (HCl) with rapid cooling to below 10° C. There was an appreciable amount of black magnetite on the magnetic stirring bar.

(iv) The suspension from step (iii) was then centrifuged for 1 hour at 5° C. and 13,500 rpm in a DuPont Sorvall RC-5B refrigerated superspeed centrifuge. An appreciable amount of black magnetite was collected at the bottom of the centrifuge tube.

(v) The supernatant liquid collected from the tubes was passed through a 0.2 micron Nalgene filter. The filter was gray, indicating that the centrifuge allowed a small fraction having a particle diameter greater than 0.2 micron to remain in suspension.

(vi) A 20 ml sample of the above was fractionated in a column (5 centimeter (cm) diameter, 40 cm length) packed with Sepharose, CL4B (Pharmacia), using a Tris buffer (3.075 g Tris base, 6.25 g NaCl, 24 ml of 1N HCl diluted to 1 liter) as the eluant. The flow rate was 4 ml per minute and a brown fraction was left at the upper part of the column. The total volume obtained in the fractionation collector was 90 ml.

(vii) The middle 50 ml of the product from step (vi) was dialyzed in the same Tris buffer using a dialysis membrane with a molecular weigh cutoff of 6000-8000 daltons. Dialysis was carried out at 5° C.

(viii) After 24 hours, the material was removed from the dialysis bag and concentrated in an Amicon diafiltration cell using a YM10 Diaflo filter (molecular weight cutoff of 10,000 daltons) and 25 pounds per square inch of argon gas. The purified suspension was stored at 5° C. and was now ready for particle size and magnetic characterization.

EXAMPLE 2

In this example, magnetite particles were prepared according to the Franklin Institute method [Kronick et al., J. Biochem. Biophys. Meth. 12:73-80 (1986)]. This method utilizes the same ingredients as described in Example 1 but with a reverse order of mixing. Here, the iron salt-dextran solution mixture was added rapidly to a hot solution of sodium hydroxide.

(i) A solution of $FeCl_3.6H_2O$ (0.18 g), $FeCl_2.4H_2O$ (0.14 g) and dextran T-10 (4 g), all in 60 ml water was added to a hot (80° C.) solution of sodium hydroxide (6.2 g NaOH in 60 ml water) very rapidly while stirring with a magnetic stir bar.

(ii) The solution from step (i) was cooled rapidly to 5° C. and 13 ml of 12N HCl added so that the final pH of the solution had a value of approximately 7.

(iii) The suspension from step (ii) was centrifuged as in step (iv) of Example 1. A considerable amount of black magnetite separated and the supernatant liquid was passed through a 0.2 micron filter which turned gray indicating particles in the suspension larger than 0.2 micron.

(iv) The suspension was fractionated in a gel column and using the steps (vi through viii) as in Example 1. The suspension was stored at 5° C.

EXAMPLE 3.

A solution consisting of 5.42 percent $FeCl_3.6H_2O$ and 2.00 percent $FeCl_2.4H_2O$ was prepared. This composition has a mole ratio of ferric ion to ferrous ion of 2/1, which is the stoichiometric ratio for the formation of magnetite. Also, premixing the two salts confers stability on the mixture. Ferrous solutions form insoluble precipitates on standing. 7.01 ml of the above solution was mixed with 50 ml of 20 percent dextran (Pharmacia, T10) and the mixture was passed through a 0.2 micron filter to remove any insoluble impurities.

A 150 ml beaker of this mixture was placed into a 600 ml beaker, and 60 ml of concentrated ammonium hydroxide was placed in the space between the two beakers. The system was closed off from the atmosphere and stirred with a magnetic stirrer. After 1 hour, the solution had turned a dark burgundy color, and the pH value of the solution was 10.4. The pH of the solution was lowered to a value of 7.0 with concentrated HCl.

There was no sign of magnetite adhering to the stirring bar and filtering through 0.1 micron Nalgene (nylon) filter did not produce any residue, in contrast with Examples 1 and 2.

Excess dextran was removed by diafiltration (Amicon, PM30) using argon gas at 25 psi. Four filtrations were carried out by the process of diluting the residue in the Amicon cell with water and diafiltering to the point where the dextran level in the filtrate was below 0.2 percent.

Since virtually no iron was found in the flitrates (using Atomic Absorption analysis), the reaction gave virtually 100 percent yield.

EXAMPLE 4

This Example provides data summarizing the size and magnetic resonance data obtained with the particles prepared in Examples 1-3, above.

Table 1 compares the particle sizes, crystallite dimensions, and Magnetic Resonance Relaxivities of the magnetite-dextran particles prepared according to the above examples. The sizes determined by lattice fringe imaging are the fundamental crystallite sizes independent of the amount of absorbed dextran. The methods of the present invention, embodied in Example 3, yield populations with the smallest diameters and with very narrow size distributions. The diameters determined by Laser Light Scattering includes the thickness of the dextran shell and they are all approximately the same. However, the diameters of the particles produced in the present invention show a narrow size distribution. The Transmission Electron Micrographs for particles prepared by the methods of Examples 1 and 2 were difficult to interpret because of severe particle clumping. However, the particles of the present invention, while showing aggregation, were still very well dispersed. See FIG. 1

TABLE 1

| Example | PARTICLE SIZE | | | CRYSTALLITE SIZE Lattice Fringe Imaging | | RELAXIVITY $R_2/R_1$ |
|---|---|---|---|---|---|---|
| | TEM[1] (nm) | LASER LS[2] d (nm) | σ | d (nm) | σ | |
| 1 | 5-30 | 32 | 17.4 | 8.1 | 2.4 | 4 (Lit.)[3] |
| 2 | 5-20 | 36 | 12 | 4.6 | 0.6 | 3.5 |
| 3 | 2-10 | 34 | 1.6 | 4.1 | 0.25 | 5.5 |

MR MSRTS: 40° C., 0.47 Tesla (20 MHZ for Protons).
[1]TEM = Transmission Electron Microscope.
[2]LASER LS = LASER Light Scattering.
[3]Josephson et al., op. cit., 651.

The ratio of the magnetic resonance relaxivities $(R_2/R_1)$ is an indication as to the value of the compound as a negative imaging agent. The composition of the present invention has a large $R_2$ value, indicating that this composition is an excellent negative imaging agent. A future commercial material (AMI-25, Advanced Magnetics Inc.) has a ratio of 4 for an average particle size of 72 nm.

EXAMPLE 5

This Example illustrates the use of a gel matrix containing the iron salts in suspension and which allows the use a strong caustic base solution instead of ammonia vapor.

The following was mixed into a 10 percent solution of gelatin derived from pigskin (with an isoelectric point of 8.5). The iron salts were dissolved at a temperature of 45° C. at which the gelatin is liquid.

To 10 ml of gelatin solution was added 0.076 g of ferric chloride.$6H_2O$ and 0.028 g ferrous chloride.$4H_2O$. The solution was placed into a test tube and cooled to room temperature at which point it formed a rigid gel. It was overlayered with 10 ml of a 10 percent NaOH solution and placed into a refrigerator (at 4° C.) overnight.

18 hours later, the first 12mm of gelatin had turned to a characteristic red-brown color typical of small magnetite particles. The excess alkali was washed off the surface of the solidified gelatin, and the temperature of the gelatin was raised to 45° C. to melt the gelatin. The liquid gelatin was diluted to 1 percent gelatin so that it would remain liquid at room temperature, and filtered through a 0.2 filter. No residue was retained by the filter.

EXAMPLE 6

This example is similar to Example 5 except that polyvinyl alcohol (PVA; DuPont Elvanol 71-30) was used instead of gelatin.

A small amount of boric acid was added to the iron salt-PVA mixture. This causes the PVA to gel when alkali is added. After overlayering with 10 percent sodium hydroxide and storing overnight at room temperature, the presence of magnetite, as evidenced by the characteristic red-brown color, could be detected in the upper 1cm of the solidified gel. This gel system was liquified by mixing the solidified gel with dilute acetic acid and tested for the presence of large particles by filtering through a 0.2 filter. None were detected.

The foregoing specification, including the specific embodiments and examples, is intended to be illustrative of the present invention and is not to be taken as limiting. Numerous other variations and modifications can be effected without departing from the true spirit and scope of the present invention.

I claim:

1. A process for the preparation of particles comprised of a magnetically responsive material and a dispersant, said process comprising admixing a magnetically responsive material with a dispersant to form an admixture, suspending said admixture in a gel phase and contacting said admixture in said gel phase with a base for a time period and under conditions appropriate to form a magnetically responsive material-dispersant particle.

2. The process of claim 1 wherein the magnetically responsive material is magnetite.

3. The process of claim 1 wherein the dispersant is dextran.

4. The process of claim 1 wherein said particles have a particle size range of about 2 to about 10 nm.

5. The process of claim 1 wherein said gel phase is formed by gelatin.

6. The process of claim 1 wherein said gel phase is formed by polyvinyl alcohol.

7. A process for the preparation of particles comprised of a magnetically responsive material and a dispersant, said process comprising admixing a magnetically responsive material with a dispersant to form an admixture and contacting said admixture with a base in the vapor phase to form said magnetically responsive material dispersant particle.

8. The process of claim 7 wherein said magnetically responsive material is magnetite.

9. The process of claim 7 wherein said dispersant is dextran.

10. The process of claim 7 wherein said particles have a particle size between about 2 and about 10 nm.

11. The process of claim 7 wherein said base is ammonium hydroxide.

* * * * *